(12) United States Patent
Bierganns et al.

(10) Patent No.: US 10,113,949 B2
(45) Date of Patent: Oct. 30, 2018

(54) DEVICE AND METHOD FOR DETECTING AND ANALYZING DEPOSITS

(71) Applicant: SOLENIS TECHNOLOGIES CAYMAN, L.P., Schaffhausen (CH)

(72) Inventors: Patric Bierganns, Krefeld (DE); Markus M Broecher, Mulheim an der Ruhr (DE)

(73) Assignee: SOLENIS TECHNOLOGIES, L.P., Wilmington, DE (US)

( * ) Notice: Subject to any disclaimer, the term of this patent is extended or adjusted under 35 U.S.C. 154(b) by 195 days.

(21) Appl. No.: 14/784,096

(22) PCT Filed: Apr. 16, 2014

(86) PCT No.: PCT/EP2014/057796
§ 371 (c)(1),
(2) Date: Oct. 13, 2015

(87) PCT Pub. No.: WO2014/170395
PCT Pub. Date: Oct. 23, 2014

(65) Prior Publication Data
US 2016/0076990 A1 Mar. 17, 2016

(30) Foreign Application Priority Data

Apr. 18, 2013 (EP) .................................... 13164319

(51) Int. Cl.
*G01N 17/02* (2006.01)
*G01N 17/00* (2006.01)
(Continued)

(52) U.S. Cl.
CPC ........... *G01N 17/008* (2013.01); *G01N 27/27* (2013.01); *G01N 29/041* (2013.01); *G01N 2291/045* (2013.01); *G01N 2291/263* (2013.01)

(58) Field of Classification Search
CPC ...... G01N 17/008; G01N 17/02; G01N 27/27; G01N 29/041; G01N 2291/045;
(Continued)

(56) References Cited

U.S. PATENT DOCUMENTS

| 6,019,000 A | 2/2000 | Stanke et al. |
| 2007/0006656 A1 | 1/2007 | Batzinger et al. |

(Continued)

FOREIGN PATENT DOCUMENTS

| CN | 101189494 B | 9/2010 |
| CN | 102066935 A | 5/2011 |

(Continued)

OTHER PUBLICATIONS

Jean-Pierre Poyet et al., "Real-Time Method for the Detection and Characterization of Scale", SPE 74659, pp. 1-10, 2002.
(Continued)

*Primary Examiner* — Manish S Shah
*Assistant Examiner* — Rose M Miller
(74) *Attorney, Agent, or Firm* — LKGlobal | Lorenz & Kopf, LLP

(57) ABSTRACT

The present invention relates to a device for detecting deposits in a reflection area inside a liquid-bearing system comprising an ultrasonic transducer for emitting an ultrasonic emission signal towards the reflection area and a first detection means for detecting an ultrasonic reflection signal obtained by reflection of the ultrasonic emission signal in the reflection area, wherein a second detection means is disposed in the reflection area, the second detection means being configured to detect a specific kind of deposit.

14 Claims, 4 Drawing Sheets

(51) Int. Cl.
*G01N 27/27* (2006.01)
*G01N 29/04* (2006.01)

(58) Field of Classification Search
CPC ........... G01N 2291/263; G01N 29/043; G01N 29/44; G01N 29/07; G01N 29/024; G01N 29/222; G01N 2291/0231; G01N 2291/0289; G01N 2291/044; G01N 2291/101; G01N 2291/2636; G01N 2291/011; G01N 2291/0246; G01N 2291/0251; G01N 2291/02656; G01N 2291/02854
USPC .......................... 73/602, 598, 597, 627, 629
See application file for complete search history.

(56) References Cited

U.S. PATENT DOCUMENTS

| | | |
|---|---|---|
| 2009/0314445 A1 | 12/2009 | Shevchenko et al. |
| 2011/0283780 A1 | 11/2011 | Bosbach et al. |
| 2012/0222484 A1 | 9/2012 | Flister et al. |
| 2014/0177673 A1* | 6/2014 | Bliss ...................... G01N 25/18 374/165 |

FOREIGN PATENT DOCUMENTS

| | | |
|---|---|---|
| CN | 102257376 A | 11/2011 |
| CN | 102483393 A | 5/2012 |
| JP | 2002277448 | 9/2002 |
| WO | 9927333 A1 | 6/1999 |
| WO | 2009141135 | 11/2009 |
| WO | 2014170395 A1 | 10/2014 |

OTHER PUBLICATIONS

International Search Report, PCT/EP2014/057796, pp. 1-3, dated Jul. 14, 2014.
State Intellectual Property Office of the People's Republic of China, Office Action in Chinese Patent Application No. 20148002175.2 dated Apr. 24, 2017.

* cited by examiner

DEVICE AND METHOD FOR DETECTING AND ANALYZING DEPOSITS

BACKGROUND

The present invention relates to a device and a method for detecting and analyzing deposits.

Industrial plants, like power plants, steel mills, pulp or paper making plants, usually comprise means for conducting or storing fluids, e.g. pipe lines or fluid containers. It is a known issue that organic and inorganic matter deposits on the inner walls of these means for conducting or storing fluids, whereby an accumulation of fouling or scaling deposits at least partially blocks the flow through the conducting means. In this way, conducted or stored fluids may become contaminated. This is an unwanted occurrence that causes a number of operational problems such as plugging of equipment, inefficient usage of chemicals, increased utility costs, lost production due to downtime, corrosion, and downgraded products from increased dirt counts.

In principle, one can distinguish between fouling deposits on the one hand and scaling deposits on the other hand. Fouling deposits are organic deposits which often occur in the form of biofilms in aqueous systems. Such biofilms substantially consist of micro-organisms, e.g. bacteria, algae, fungi and protozoa. Contrary thereto, scale depositions occur from inorganic matter that have been identified include e.g. complexes of calcium (carbonate, oxalate, sulfate, silicates), aluminum (silicates, hydroxides, phosphates), barium sulfate, radioactive radium sulfate, and silicates of magnesium.

Industrial plants usually comprise multiple functional units, like boiler, heat exchanger, condenser, mixer, for instance. These multiple functional units are connected to each other, in particular in series and/or in parallel, via connection pipes and the like.

A problem of known devices for measuring fouling or scaling deposits in an industrial plant is that it is difficult to install such like measuring devices inside of the functional units because of e.g. limited installation space or excessively elevated temperatures inside the functional units. Consequently, the devices are provided usually at or in the connecting pipes between the functional units, even though the temperatures inside of the functional units are regularly higher than in the connecting pipes, in particular when the functional unit comprises e.g. a boiler. This is disadvantageous for the quality of the measurements because higher temperatures increase the growth of fouling, so that there is frequently a higher accumulation of deposits inside the functional units than inside of the connection pipes. Consequently, the results measured in the connecting tubes are falsified and the thickness of deposits in the relevant areas cannot be accurately determined.

In order to avoid the accumulation of fouling deposits and in particular the growth of biofilms, biocides are added into the fluid concerned as countermeasures. Scaling deposits can be removed by adding chemical deposit control agents based on homopolymers, co-polymers and terpolymers of acrylic acid, methacrylic acid, maleic acid and aspartic acid. Furthermore the chemical deposit control agents can be based on organic phosphonates and their derivatives, as well as on polyphosphates. The dosage of these biocides and chemical deposit control agents has to be accomplished very carefully and conservative because they are very expensive and pose a health hazard.

SUMMARY

It is therefore an object of the present invention to provide a device and a method for detecting deposits in order to allow for an economically and ecologically improved treatment of the liquid bearing system. For ecological and economic reasons, it is thereby desirable to reduce the dosage of the biocides and/or chemical deposit control agents to a minimum.

The object of the present invention is achieved by a device for detecting deposits, in particular fouling and/or, scaling deposits, in a reflection area inside a liquid-bearing system comprising an ultrasonic transducer for emitting an ultrasonic emission signal towards the reflection area and a first detection means for detecting an ultrasonic reflection signal obtained by reflection of the ultrasonic emission signal in the reflection area, wherein a second detection means is disposed in the reflection area, the second detection means being configured to detect a specific kind of deposit.

According to the present invention, it is thereby advantageously possible to distinguish a specific kind of deposit from another kind and to quantify the specific kind of de-posit which has been detected by the second detection means. In particular, the specific kind of deposit may be one of scaling or fouling deposit, organic or inorganic deposit, biotic or abiotic deposit, living or dead deposit. A deposit is considered "alive" or "living" when the deposit contains organisms with signaling and self-sustaining processes. Otherwise, the deposit is considered "dead" or "inanimate", if such signaling and self-sustaining processes are not detectable, if such functions have ceased and/or if the constituents of the deposit lack such functions. The first detection means allows for the analysis of the deposit in the reflection area in order to characterize the physical properties such as softness of the deposit, spatial extension of the deposit in the reflection area parallel and perpendicular to the traveling direction of the reflection signal. Hereby, it is in particular advantageously possible to quantify the deposit. Additionally, the second detection means allows for the detection of a specific kind of deposit, which means that a specific kind of deposit is distinguishable from another specific kind of deposit. In particular, it is herewith possible to detect if the deposit is living, which means that the deposit may be for example a biofilm consisting of living organisms or dead or inanimate, where the latter refers to at least one of dead organisms, inanimate bio-material or other non-living organic or inorganic substances. Combining the analysis of the physical properties obtained from the first detection means with the analysis of the second detection means, in particular regarding the distinction of the specific kind of deposit from other kinds of deposits and/or their liveliness, allows for the characterization of the specific kind of deposit. Such a characterization includes, for example, the identification and quantification of the specific kind of deposit. Herewith, the fouling and/or scaling deposits can be detected in a timely and reliable fashion. The combined effect of detecting, both, the specific kind of deposit and the physical properties of the deposit is that it is possible to perform a targeted treatment of the liquid bearing system such that certain requirements on purity standards on the liquid bearing system are fulfilled. In particular, the treatment of the liquid bearing system can be targeted to the specific deposit such that the accumulation of fouling deposits, in particular the growth of biofilms, is efficiently avoided. Additionally, the advantage of providing the device with, both, the first detection means and the second detection means as described above over a device with only a second detection means is that it is possible to detect a deposit also in the case when the deposit is dead. With the treatment being targeted to the deposit it is therefore possible to perform the treatment in an economically as well as ecologically effective fashion. Thereby the protection of the environment can be improved, whereas the costs of treatment of the liquid bearing system can be considerably reduced at the same time. Also, for ecological reasons, it is possible according to the present invention to reduce the dosage of the biocides and/or chemical deposit control agents to a minimum.

In particular, the wording "deposits" in the sense of the present inventions stands for any kind of organic or inorganic contaminants and deposits that occurs in liquid-bearing systems, like e.g. circuits, pipes or containers. Such like deposits occur e.g. in the form of films (also called "fouling"). These are formed primarily in aqueous systems at the interface with a solid phase. In case of micro-organisms caused films, they consist of a slimy layer in which micro-organisms (e.g. bacteria, algae, fungi, and protozoa) are embedded. As a rule, these films contain, other than the micro-organisms, primarily water and extra-cellular polymeric substances exuded by the micro-organisms which, in conjunction with the water, form hydrogels and contain other nutrients or substances. Often, particles are included in the resulting slimy matrix that is found in the aqueous medium adjacent the interface. The films which occurs e.g. in papermaking plant are characterized by the fact that it contains a high proportion of fibers, fine substances, and inorganic pigments that are bound by the organic matrix. Such films typically are accompanied by protective exopolysaccharides ("slime", EPS) of microbiological sources and occur at the interface of these equipment surfaces and process water streams. Additionally, inorganic contaminants, such as calcium carbonate ("scale") and organic contaminants often deposit on such surfaces. These organic contaminants are typically known as "pitch" (e.g., resins from wood) and "stickies" (e.g., glues, adhesives, tape, and wax particles). According to a preferred embodiment of the present invention, the second detection means is at least one of electrochemical biosensor, optical biosensor, electronic biosensor, piezoelectric biosensor or gravimetric biosensor or other biosensor. A biosensor typically consists of a biological transducer or bio-transducer, for example having a bio-recognition component such as a receptor. The biological transducer interacts with a biological component such as a living cell of the deposits. Thereby, it is advantageously possible to recognize, for example, the kind of deposit via the detection of the electrochemical activity of the deposits. In this way it is possible to determine whether the deposit comprises living organisms. The biological transducer then generates a detection signal, for example a liveness detection signal comprising information about whether the deposits contain living organisms. In particular the liveness detection signal is generated depending on an interaction between the deposits and a receptor of the biological transducer. The detection signal is then further processed by an electronic system of the biosensor. Thus, it is advantageously possible to determine a covering level of the deposits in the reflection area and/or to determine the liveness of the deposits in the reflection area.

According to a preferred embodiment of the present invention, the second detection means is configured to generate a liveness detection signal comprising liveness information about the deposits. It is herewith advantageously possible to determine a covering level of the deposits in the reflection area and/or to determine the liveness of the deposits in the reflection area, whereby at the same time the physical properties of the deposit may be analyzed using the first detection means. It is thus advantageously possible to distinguish a specific kind of deposit from other kinds of deposits. For example, it is possible to determine if the deposit is a living deposit, for example a biofilm in the liquid bearing system. The liveness information comprises information about whether the specific kind of deposit, in particular the biofilm, comprises living organisms. The combined information the physical properties of the biofilm and whether the biofilm comprises living organisms allows for a targeted treatment of the liquid bearing system.

According to a preferred embodiment of the present invention, the device comprises an analyzing unit configured to determine, depending on the liveness detection signal, a covering level of the deposits in the reflection area and/or the liveness of the deposits in the reflection area. It is herewith advantageously possible to operate the device in different operation modes. For example, the analyzing unit may indicate the reaching of a given bio-film covering level in a threshold mode, whereas the whole development of bacterial covering in the reflection area may be monitored in a measuring mode. Thereby it is advantageously possible to monitor a biofilm in the liquid bearing system in real-time in order to allow for a timely cleaning treatment of the liquid bearing system depending on the liveness detection signal.

According to a preferred embodiment of the present invention, the biosensor is an electrochemical biosensor configured to generate the liveness detection signal depending on a measured electrochemical activity of the deposits. It is herewith advantageously possible to provide a reliable detection of a specific kind of deposit, such as a biofilm. In particular, it is herewith advantageously possible to determine whether the biofilm is living, i.e. comprises living organisms. In this way, it is possible to detect the specific kind of deposits, in particular the liveness of the deposits, with high sensitivity.

According to a preferred embodiment of the present invention, the analyzing unit is configured to analyze the reflection signal in order to determine whether deposits are located in the reflection area and/or to determine the type and/or the thickness of a layer of deposits in the reflection area. It is herewith advantageously possible to measure physical properties of the deposits, for example whether the deposit consists of comparatively soft or hard matter, wherein the softness is typically quantified by the elastic modulus. The physical properties of the deposits in the reflection area are determined by means of evaluating the time-domain reflective signal of the reflection area. Moreover, it is possible to measure the deposit covering in the reflection area. The measured distance is compared to a reference distance which has been measured in an initial calibration measurement step without any deposits onto the reflection area. Alternatively, a reference measuring unit may be employed for this purpose. The difference between the measured distance and the reference distance is a measure for the thickness of the deposition. The further advantage of providing the device with the first detection means in addition to the second detection means as described above over a device with only a second detection means is that it is possible to detect a deposit also in the case when the deposit is dead.

According to a preferred embodiment of the present invention, the device has a first measuring unit comprising the ultrasonic transducer and the first detection means, wherein the device has a second measuring unit comprising the second detection means disposed in the reflection area, wherein the first measuring unit and the second measuring unit are detachably connected to the liquid-bearing system in such a manner that the first measuring unit and the second measuring units are located on opposite sides of the liquid-bearing system. It is herewith advantageously possible to provide a device for the detection of scaling and/or fouling deposits that can be flexibly employed in a wide variety of components of liquid bearing systems, for example pipelines, wherein the costs of operation may be considerably reduced. Furthermore, the detachable connection allows for easy exchange, for example during maintenances of the liquid bearing system or the detection components.

According to a preferred embodiment of the present invention, the device has a first reference measuring unit comprising a further ultrasonic transducer and a further first detection means, wherein the device has a second reference measuring unit comprising a further reflection area and a further second detection means disposed in the further reflection area, wherein the analyzing unit is configured to determine properties of the deposits in the reflection area depending on reference information provided by the first and/or second reference measurement unit. It is herewith advantageously possible to measure the distance by comparing it to a reference distance which is measured in a calibration measurement step using the first and/or second reference measuring unit without any deposits onto the reflection area. The real distance between the ultrasonic transducer and the reflective area changes e.g. with the temperature or the pressure inside the fluid vessel. Therefore, the current distance between the ultrasonic transducer and the reflective area at the time of measurement can be accurately defined by a simultaneous measured reference distance. Consequently, the measurement of the thickness of the deposits does not comprise an unknown offset depending on operational conditions, like pressure and temperature. In this way the physical properties of the deposits may be determined with comparatively high sensitivity.

Another subject of the present invention is a method for detecting fouling and/or scaling deposits in a reflection area inside a liquid-bearing system, comprising a first step of emitting an ultrasonic emission signal towards the reflection area by an ultrasonic transducer, a second step of detecting an ultrasonic reflection signal obtained by reflection of the ultra-sonic emission signal in the reflection area by first detection means and a third step of detecting a specific kind of deposit by a second detection means disposed in the reflection area.

According to the present invention, it is thereby advantageously possible to combine the analysis of the physical properties obtained from the first detection means with the analysis of the second detection means. In particular a distinction of the specific kind of de-posit from other kinds of deposits can be made, which may include liveliness of the deposits. The wording liveliness of the deposits includes the information whether the deposits consist of living organisms such as bacteria. Thus, it is possible to characterize the specific kind of deposit, which includes for example the identification and quantification of the specific kind of deposit. Further, the fouling and/or scaling deposits can be detected in a timely and reliable fashion. The combined effect of detecting, both, the specific kind of deposit and the physical properties of the deposit is that it is possible to perform a targeted treatment of the liquid bearing system such that certain requirements on purity standards on the liquid bearing system are fulfilled. Additionally, the advantage performing the steps of, both, the determination of physical properties of the deposits and the detection or identification of a specific kind of deposit as described above over a method wherein only the specific kind of deposit is detected is that it is possible to detect a deposit also in the case when the deposit is dead. The method according to the present invention allows for the combination of at least two different measuring methods for the detection of scaling and/or fouling deposits, in particular of such deposits contained in a fluid pipe of the liquid bearing system. This allows for an optimization of the cleaning treatment of the fluid pipes. According to the second step, physical properties such as the quantity determined from the thickness of the layer of deposits may be measured, wherein in the third step the specific kind of deposit probed in the second step may be distinguished from other kinds of deposits in the third step. In particular, the second and third step may be performed simultaneously. It is thereby particularly preferred to determine whether the deposit is living, i.e. comprises living organisms.

According to a preferred embodiment of the present invention, in the third step the liveness of the deposits is detected by at least one of an electrochemical biosensor, optical biosensor, electronic biosensor, piezoelectric biosensor, gravimetric biosensor or other biosensor. It is herewith advantageously possible to detect biological features of the depos-its, in particular such as whether the deposit is living or dead. In particular, it is possible to determine whether the deposits contain living organisms and/or which type of living organ-isms are included in the deposits. Such information may be employed to perform a target specific cleaning treatment of the liquid bearing system, thereby reducing the dosage of biocides and/or chemicals used during the cleaning treatment.

According to a preferred embodiment of the present invention, the liveliness detection in the third step comprises a first detection step, wherein the deposits are recognized by a biological transducer of the biosensor, a second detection step, wherein a liveness detection signal is generated depending on an interaction between the deposits and a receptor of the biological transducer, a third detection step, wherein the liveness detection signal is processed by an analyzing unit in order to determine a covering level of the deposits in the reflection area and/or to determine the liveness of the deposits in the reflection area. It is herewith advantageously possible to determine whether the deposits contain living organisms and/or which type of living organisms are included in the deposits. Such information may be employed to perform a target specific cleaning treatment of the liquid bearing system, thereby reducing the dosage of biocides and/or chemicals used during the cleaning treatment.

According to a preferred embodiment of the present invention, in the second detection means is an electrochemical biosensor, wherein in the third step an electrochemical activity of the deposits is measured by the biosensor and the liveness detection signal is generated depending on the measured electrochemical activity of the deposits. It is herewith advantageously possible to determine a covering level of the deposits in the reflection area and/or to determine the liveness of the deposits in the reflection area, whereby the physical properties of the deposit is analyzed at the same time. It is thus advantageously possible to distinguish a specific kind of deposit from other kinds of deposits. For example, it is possible to determine if the deposit is a living deposit, for example a biofilm in the liquid bearing system. The liveness information comprises information about whether the specific kind of deposit, in particular the biofilm, comprises living organisms. The combined information the physical properties of the biofilm and whether the biofilm comprises living organisms allows for a target specific cleaning treatment of the liquid bearing system. Thereby the dosage of biocides and/or chemicals used during the cleaning treatment can be effectively reduced.

According to a preferred embodiment of the present invention, in the second step, the reflection signal is analyzed by the analyzing unit in order to determine whether deposits are located in the reflection area and/or to determine the type and/or the thickness of a layer of deposits in the reflection area. It is herewith advantageously possible to measure physical properties of the deposits. For example it is possible to determine with such a measurement whether the deposit consists of comparatively soft or hard matter. The softness or hardness may typically be quantified by the elastic modulus. The physical properties of the deposits in the reflection area are determined by means of evaluating the time domain reflective signal of the reflection area. The physical properties of the deposits are determined depending the running time of the ultrasound signal, the intensity of the reflection signal and/or the frequency of the reflection signal compared to the frequency of the emission signal. The further advantage of providing the device with the first detection means in addition to the second detection means as described above over a device with only a second detection means is that it is possible to detect a deposit also in the case when the deposit is dead.

According to a preferred embodiment of the present invention, in a fourth step, the liquid of the liquid-bearing system is treated depending on the detected liveness of the deposits, depending on the type and/or the thickness of a layer of deposits in the reflection area and/or depending on whether deposits are located in the reflection area. It is herewith advantageously possible to perform a treatment of the liquid bearing system being targeted to the deposit in an economically as well as ecologically effective way. Thereby the protection of the environment can be improved, whereas the costs of treatment of the liquid bearing system can be considerably reduced at the same time.

These and other characteristics, features and advantages of the present invention will become apparent from the following detailed description, taken in conjunction with the accompanying drawings, which illustrate, by way of example, the principles of the invention. The description is given for the sake of example only, without limiting the scope of the invention. The reference figures quoted below refer to the attached drawings.

DETAILED DESCRIPTION

Figure 1:
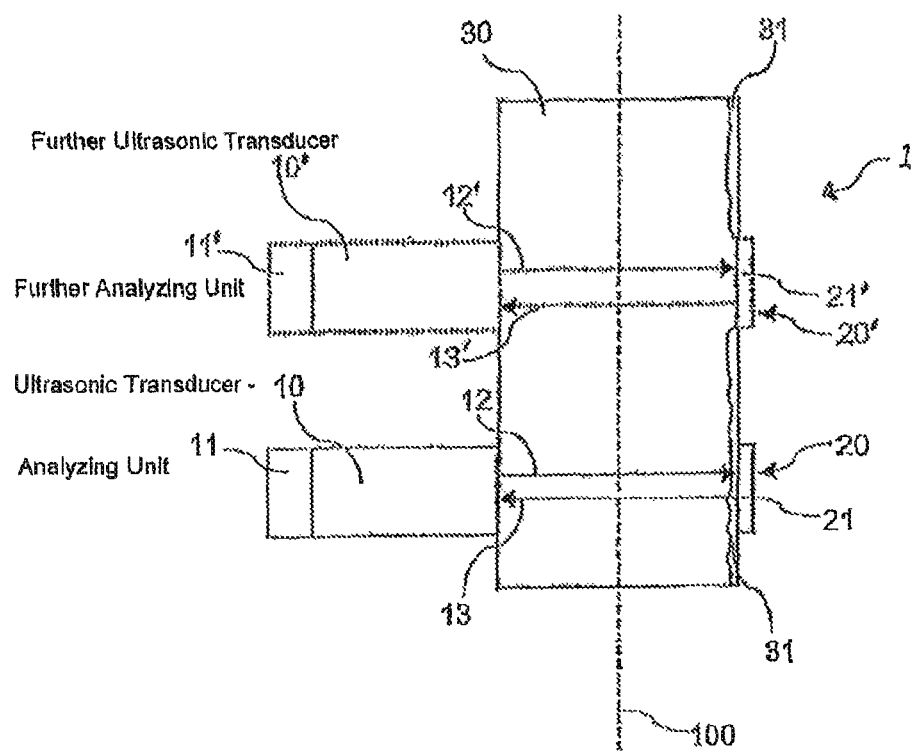
FIG. 1 illustrates schematically a device for detecting scaling and/or fouling deposits according to the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

Where an indefinite or definite article is used when referring to a singular noun, e.g. "a", "an", "the", this includes a plural of that noun unless something else is specifically stated.

Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described of illustrated herein.

In FIG. 1, a device 1 for detecting scaling and/or fouling deposits 31 according to the present invention is illustrated schematically. The device 1 advantageously allows the detection of deposits 31, in particular in fluid pipes 30, in liquid bearings systems, in particular in cooling circuits of industrial plants, like power plants, steel mills, pulp or paper making plants. The liquid may flow along a flow direction 100 within a flowing pipe 30 of the liquid bearing system. The detection of deposits 31 may include the measurement of physical properties of the deposits 31 such as density, softness in the sense of elastic modulus of the deposits 31 as well as the detection of specific kind of deposits 31 such as organic, inorganic, biological, non-biological, living or dead deposits 31. Thus, the device 1 allows a distinction of a specific kind of deposit 31 such as a biofilm comprising living bacteria or other organisms from other deposits 31 such as inorganic deposits 31 and furthermore allows the determination of physical properties of the specific kind of deposit 31 at the same time.

The device 1 may be detachably connected to a fluid pipe 30 of the liquid bearing system in order to detect scaling and/or fouling deposits 31 in a reflection area 20 inside a inside the fluid pipe 30. The device 1 comprises an ultrasonic transducer 10 for emitting an ultrasonic emission signal 12 towards the reflection area 20 and a first detection means 10 for detecting an ultrasonic reflection signal 13 obtained by reflection of the ultrasonic emission signal 12 in the reflection area 20. The ultrasonic transducer 10 and the first detection means 10 may be either incorporated into one unit 10 or alternatively consist of separate units, wherein one unit is configured to emit the ultrasonic emission signal 12 and the other unit is configured to detect the ultrasonic reflection signal 13. Furthermore, the device 1 comprises a second detection means 21 for detecting a specific kind of deposit 31, wherein the second detection means 21 is disposed in the reflection area 20. By disposing the second detection means 21 in the reflection area 20 it is advantageously possible to detect the same deposit 31, which is, in particular simultaneously, probed by the first detection means 10 by detecting the second reflection signal 13 in order to determine the physical properties of the deposits 31. The second detection means 21 is in particular configured to generate a detection signal comprising information which enable the distinction of the specific kind of deposit 31 from other kinds of deposits 31. For example, the second detection means 21 may comprise a biosensor 21, in particular an electrochemical biosensor, optical biosensor, electronic biosensor, piezo-electric biosensor, gravimetric biosensor and/or other biosensor. In particular, the second detection means 21 or biosensor 21 is configured to generate a liveness detection signal comprising liveness-information about the deposits. Additionally, the device may comprise an analyzing unit 11 configured to determine, depending on the liveness detection signal, a covering level of the deposits in the reflection area and/or the liveness of the deposits in the reflection area. It is particularly preferred according to the present invention that the second detection means 21 comprises an electrochemical biosensor 21 configured to generate the liveness detection signal depending on a measured electrochemical activity of the deposits 31.

According to a preferred embodiment of the present invention the second detection means 21, and in particular the further second detection means 21', are configured to detect whether the deposit 31, in particular the biofilm 31, is living or dead. For example, the second detection means 21 comprises a biosensor having a biological transducer which generates a second detection signal depending on an interaction between a receptor of the biological transducer and the deposits 31, in particular the biofilm or fouling deposits. The ultrasound emission signal 12 and reflection signal 13 may alternatively be analyzed to determine the velocity of the liquid in the liquid bearing system. The detection of the physical properties, such as the density, of the deposit is based on an analysis of the reflection signal 13, which is being reflected from the reflection area 20. In particular, the deposits 31 in the reflection area 20 may change the reflection signal 13, in particular the run-time, the intensity and/or frequency of the reflection signal 13, as compared to the emission signal 12. It is thereby advantageously possible to recognize the kind of deposits 31, i.e. whether the deposits 31 comprise organic or inorganic, biological or non-biological as well as living or dead deposits 31. This enables the distinction of a specific kind of deposit 31 from other kinds of deposits 31 and the determination of the amount of the specific kind of deposit 31 at the same time.

It is preferred according to the present invention, that the device 1 has a first reference measuring unit comprising a further ultrasonic transducer 10' and a further first detection means 10', and in particular a further analyzing unit 11', wherein the device 1 has a second reference measuring unit comprising a further reflection area 20' and a further second detection means 21' disposed in the further reflection area 20', wherein the analyzing unit 11 is configured to determine properties of the deposits 31 in the reflection area 20 depending on reference information provided by the first and/or second reference measurement unit. The further ultrasonic transducer 10' is configured to emit a further ultrasonic emission signal 12' towards the further reflection area 20'. The further first detection means 10' is configured to detect a further ultrasonic reflection signal 13' obtained by reflection of the further ultrasonic emission signal 12' in the further reflection area 20'. In this way, it is advantageously possible to measure the distance between the reflection area 20 and the ultrasonic transducer 10 by comparing it to a reference distance between the further ultrasonic transducer 10' and the further reflection area 20'. The further reflection area 20' may thereby be kept clean from any deposits 31, for example by cleaning the further reflection area 20' with the further emission signal 12' emitted by the further ultrasound transducer 10'. The real distance between the ultrasonic transducer 10 and the reflection area 20 changes e.g. with the temperature or the pressure inside the fluid pipe 30. Therefore, the distance between the ultrasonic transducer 10 and the reflection area 20 at the time of measurement can be accurately determined by the simultaneous measured reference distance described above. Consequently, the measurement of the thickness of the deposits 31 does not comprise an unknown offset depending on operational conditions, like pressure and temperature such that the physical properties of the deposits 31 may be determined with comparatively high sensitivity.

Figure 2:
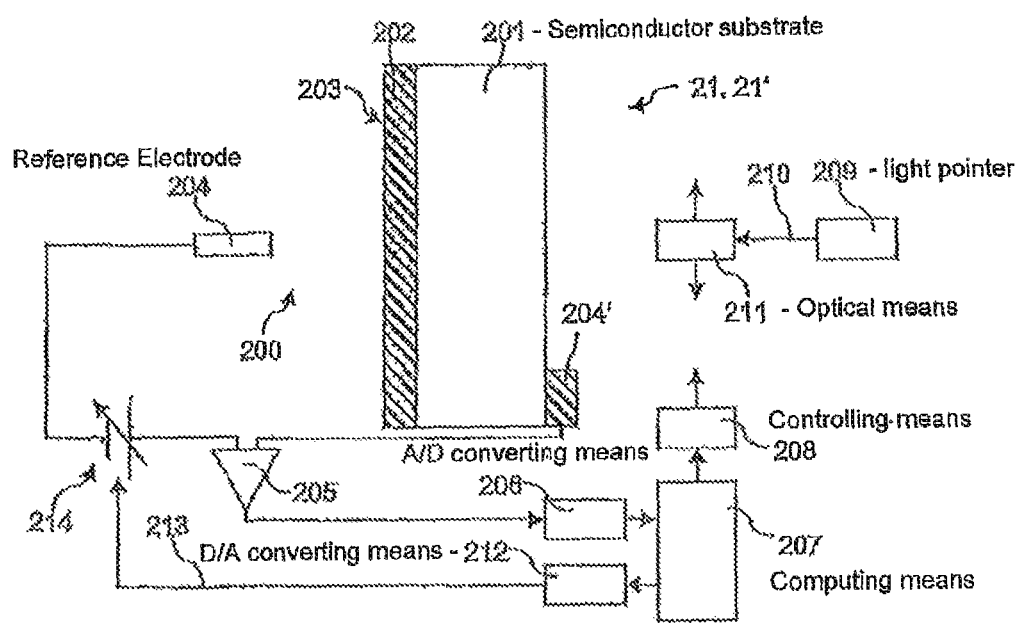
FIGS. 2 to 4 show schematically several embodiments of a second detection means of a device according to the present invention.
Figure 3:
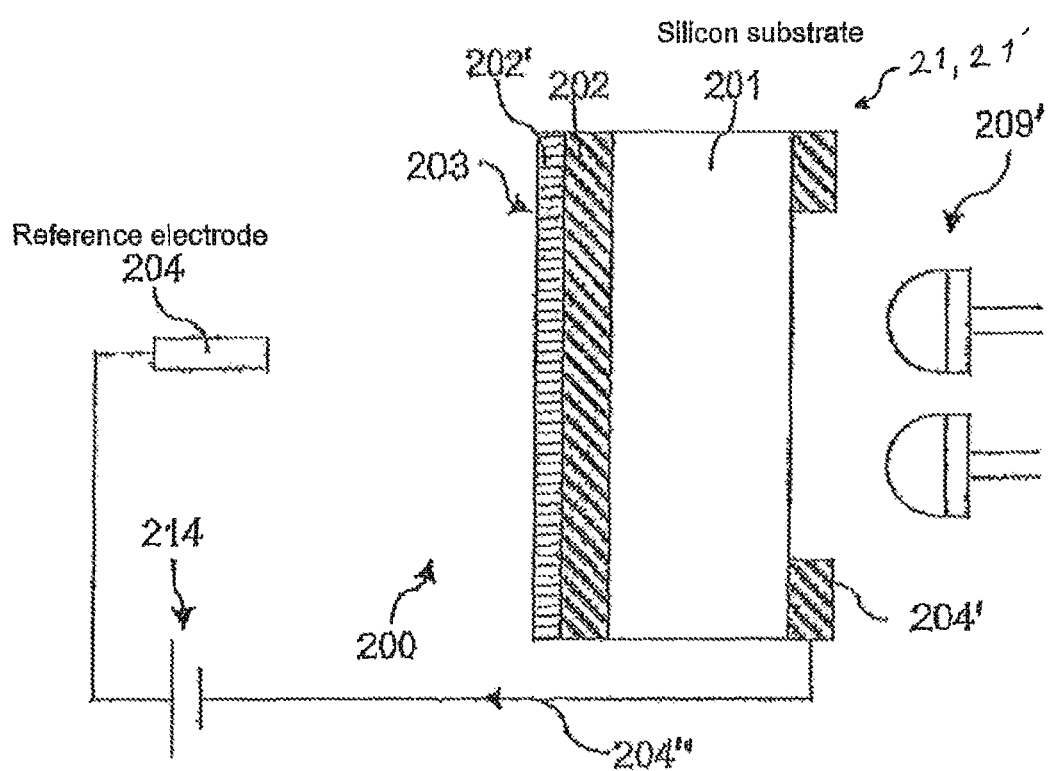
Figure 4:
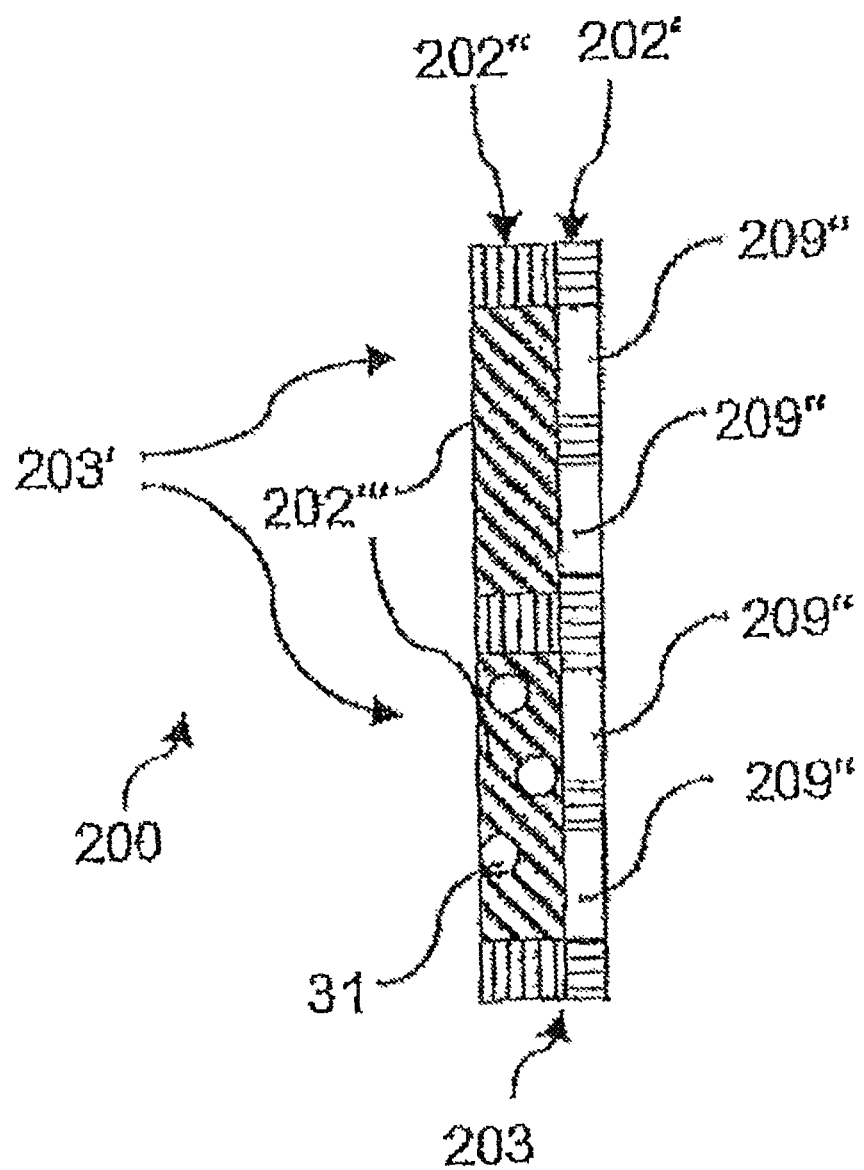

In FIGS. 2 to 4 several embodiments of a second detection means of a device 1 according to the present invention are shown schematically. Preferably, the descriptions of the embodiments described with reference to FIGS. 2 to 4 also apply to the further second detection means 21'. Here, the second detection means 21 is a chemical imaging sensor 21, which is herein also called microphysiometer 21 or light-addressable potentiometric sensor (LAPS). Preferably, a semiconductor-based chemical imaging system 11, 21, which comprises an analyzing unit 11 and/or the second detection means 21, is configured to produce a detection signal for visualization of a two-dimensional distribution of chemical species 31 or deposits 31 in contact with a sensing surface 203 of the second detection means 21. Preferably, the chemical imaging system 11, 21 is integrated on a chip-card, preferably a wafer.

In FIG. 2, the second detection means 21 has an electrolyte-insulator-semiconductor (EIS) structure comprising a semiconductor substrate 201 and an insulating means 202 disposed on the semiconductor substrate 201, in particular silicon. Preferably, a direct current (dc) voltage is applied to the semiconductor substrate 201 by a voltage generating means 214 via a contact electrode 204', so that a depletion layer (not shown) is induced in the substrate 201. In particular, it has been found that the depletion layer is dependent on a surface potential at the sensing surface 203, which varies with a pH value of a solution 200, preferably an electrolyte solution 200. The pH value is a measure for hydrogen concentration or ionic concentration of the electrolyte solution. In particular, the solution includes the chemical species, here also called analytes 31 or deposits 31, in contact with the sensing surface 203. Preferably, the second detection means 21 comprises a reference electrode 204, which is in contact with the solution 200 and the contact electrode 204', which is in contact with the semiconductor substrate 201. Here, a capacitance of the depletion layer is read out in the form of a photocurrent 204" (see FIG. 3), in particular an alternating current (ac). Here, the photocurrent 204" is induced in the substrate 201 by illuminating the semiconductor substrate 201 with a modulated light beam 210 of a light pointer 209, preferably a laser 209. Here the modulated light beam 210 is a laser beam 210. In this way, the surface potential, and thus, the pH value or the ionic concentration of the solution is determined by measuring a difference between a first potential measured by the reference electrode 204 and a second potential measured by the contact electrode 204'. Preferably, the measured photocurrent 204" is amplified by an amplification means 205 and directed via an analog-to-digital converting means 206 to a computing means 207.

Preferably, a focused laser beam 210 is generated by optical means 211, wherein the optical means 211 are configured to scan the sensing surface 203 or sensing area 203. Preferably, the laser light source 209 is installed together with the optical means 211, in particular a focusing optics beneath the sensor stage. Here the optical means 211 is configured for positioning the laser beam 210 at each light point 209" in the sensing surface 203.

Herein, the light point 209", which is illuminated by the light pointer 209, is also called measurement spot 209" (see FIG. 4). Preferably, the position of the laser beam 210 on the sensing surface 203 is controlled by a controlling means 208, which operates the optical means 211 depending on a signal received from the computing means 208 and/or a feedback signal from the optical means 211.

Preferably, the computing means 207 generates a voltage control signal 213, which is in particular converted via a digital-to-analog converting means 212, for controlling the dc voltage generated by the voltage generating means 214. Preferably, the applied dc voltage and the position of the laser beam 210 are both controlled by the computing means 207, wherein the computing means 207 is configured for carrying out the measurement of the photocurrent 204" in a synchronized manner. In particular, the photocurrent 204" is measured at each measurement spot 209" separately, wherein preferably a map of the two dimensional distribution of the chemical species 31 on the sensing surface 203 is generated depending on the separate measurements at each measurement spot 209". It has been found that the spatial resolution of the sensing system 21, 11 depends on several parameters such as the thickness of the sensing plate 202, 202' and the diffusion length of minority carriers in the semiconductor 203. Preferably, the second detection means 21 is configured to resolve a line pattern with a width of 1 to 10 micrometers, preferred, 3 to 7 micrometers, even more preferred 5 micrometers. Preferably, the measuring rate is 100 pixels per second.

Preferably, the sensing surface 203 comprises a polymer and/or is provided with a micro-structured material. Preferably, the micro-structured material comprises porous silicon, wherein macropores with an average diameter of less than 10 micrometers, preferred less than 5 micrometers, even more preferred approximately 1 micrometer, are formed. Hereby it is advantageously possible to improve the adhesion of biological cells 31 on the sensing surface 203 and/or enable continuous measurement of the surface potential, pH value and/or ionic concentration of the solution 200 and/or a change of pH value in a culture medium 200. It is thereby furthermore advantageously possible to visualize and/or quantify biochemical activities of biological systems 31 disposed on the sensing surface 203.

FIG. 3 shows an embodiment of the second detection means 21 of a device 1 according to an embodiment of the present invention. Here, the second detection means 21 is a LAPS 21, preferably a field-effect based sensor 21, in particular an ion-selective field-effect transistor (ISFET) or an electrolyte-insulator semiconductor sensor. Here, the second detection means 21 has a layered structure comprising a substrate layer 201, preferably comprising a silicon substrate 201 of a silicon wafer, in particular p-doped silicon, an insulating layer 202 comprising insulating means 202, preferably silicon oxide, and a transducer layer 202' comprising transducing means 202', preferably Ta2O5. Here, a contact electrode 204', preferably an Ohmic contact 204', preferably Al, is disposed at the rear side opposite to the sensing surface 203 along a direction perpendicular to a plane of main extension of the sensing surface 203. Preferably, the contact electrode 204' is ring shaped. Here, the contact electrode 204' provides an electrical connection to the layered structure of the second detection means 21. Preferably, the contact electrode 204' is electrically connected to a reference electrode 204, preferably an Ag/AgCl liquid junction electrode. Preferably, the reference electrode 204 and the second electrode 204' are connected to an interface electronic system 11 or analyzing unit 11 of the semiconductor-based chemical imaging system, wherein the interface electronic system 11 is configured to provide a signal to operate the second detection means 21 and/or to read out a sensor signal 204", preferably a photocurrent 204", from the second detection means 21.

Preferably, the transducing means 202' of the second detection means 21 is configured for electrochemical interaction with a deposit 31 or analyte 31 at the sensing surface 203, in a solution in contact with the sensing surface 203 and/or immobilized by immobilization means 202''' (see FIG. 4) disposed at the sensing surface 203. In particular, a surface potential is created due to the electrochemical interaction between the transducing means 202' and the analyte 31. It has been found that the surface potential depends on a concentration of the analyte 31 on the sensing surface 203 and/or in the solution 200. Preferably, the photocurrent 204" is measured depending on a position of a light point 209" or measurement spot 209" on the sensing surface 203. It is thereby advantageously possible to obtain a spatial resolution of the deposit on the sensing surface 203. Here, the second detection means 21 comprises a light pointer array 209', preferably an infrared radiation (IR) light emission diode (LED) array 209', as the light pointer 209. In particular, the IR-LED array 209' is configured to address different sensor regions or measurement spots 209" on the sensing surface 203. Preferably, a 4 times 4 IR-LED array 209' is used thereby creating sixteen measurement spots 209" on the sensing surface 203.

According to a first operating mode, the IR-LEDs are illuminated one by one in a batch mode manner that allows the measurement of all 16 measurement spots in a fixed timing sequence. It is thereby advantageously possible to provide a simpler implementation with regard to software and hardware requirements. According to a second operating mode, several measurement spots are read out in parallel. Preferably, each IR-LED of the IR-LED array 209' is associated with one measurement spot 209", wherein each IR-LED emits modulated light, wherein each IR-LED is associated with a unique modulation frequency of the modulated light. Preferably, the photocurrent 204" is generated depending on individual photocurrents having different frequencies, which are associated with each IR-LED. Due to the recording of the photocurrent 204", the information of all measurement spots 209" is advantageously available at the same time. Preferably, a fast Fourier Transform algorithm is used for the separation of the photocurrent 204" into each individual photocurrent. It is there by advantageously possible to provide a simple implementation of the second detection means 21 into the device 1.

Preferably, the second detection means 21 is a light-addressable potentiometric sensor (LAPS) or microphysiometer 21 disposed on a chip-card, wherein the light-pointer array 209' is preferably integrated with the chip-card. Herewith it is advantageously possible to allow an easy handling of different sensor chips and an easy exchange of the second detection means 21 of the device 1 depending on the deposit 31 to be measured. It is thereby advantageously possible to provide a device with a second detection means, wherein the integration of the electronic and mechanical set-up of the second detection means 21 into a single chip-card unit results in a compact design with the benefit of portability and low required space.

In FIG. 4, four measurement spots 209" are shown, which are generated by a light pointer array 209', preferably the IR-LED array 209', on the sensing surface 203. Here, a photoresist layer 202" is connected with the transducing means 202' on the sensing sur-face 203. Preferably, the photoresist layer 202" comprises an epoxy-based negative photo-resist comprising polymer, preferably SU-8. Preferably, wells 203' are created in the photoresist layer 202", wherein the wells 203' preferably have a size of approximately 6 times 13 mm$^2$. Preferably, the wells 203' are filled with an immobilization means 202''', preferably a gel 202''', in particular polyacrylamide gel. Here, a first well of the wells 203' comprises only the immobilization means 202''' and a second well of the wells 203' comprises the immobilization means 202''' and an analyte 31 or deposit 31. It is thereby advantageously possible to provide an on-chip differential set-up of the second detection means 21. Preferably, the first well of the wells 203' serves as the further detection means 21' for reference measurements. It is thereby advantageously possible to reduce external influences to the measurement, for example sensor drift, temperature and/or external pH changes. It has been found that the external influences affect both areas of the sensing surface 203 within the wells 203' and can be compensated by differential measurement. Preferably, the immobilization means 202''' comprises enzymes, cells, bacteria and/or biofunctionalized polymers. For example, immobilization means comprise a matrix entrapment in gel for creating a uniform cell distribution with a high amount of cells. Alternatively, cells are immobilized by adherent growth or covalent immobilization. Here, for example alginate, agarose or polyacrylamide gel is used as a gel matrix in the wells 203'. It is hereby advantageously possible to provide a biosensor as a second detection means 21, which is based on living cells immobilized on sensing surface 203 of a light-addressable potentiometric sensor (LAPS) 21. Preferably, the second detection means 21 is sensitive to the concentrations of nutrients metabolized by bacteria, in particular due to an extracellular acidification. Preferably, the second detection means 21 or LAPS 21 is provided on a chip, wherein the LAPS is configured for differential measurement of a nutrient concentration. It is thereby advantageously possible to reduce external influences by differential measurement.

REFERENCE SIGNS 1 device
10 ultrasonic transducer I first detection means
11 analyzing unit
12 ultrasonic emission signal
13 ultrasonic reflection signal
20 reflection area
21 second detection means
10' further ultrasonic transducer I first detection means
11' further analyzing unit
12' further ultrasonic emission signal
13' further ultrasonic reflection signal
20' further reflection area
21' further second detection means
30 fluid pipe
31 deposits
100 flow direction
200 solution
201 substrate
202 insulating means
202' transducing means
202" photoresist layer
202''' immobilization means
203 sensing surface
203' well
204 reference electrode
204' contact electrode
204" photo current
205 amplification means
206 analog-to-digital converting means
207 computing means
208 controlling means
209 light pointer
209' light pointer array
209" measurement spot
210 light beam
211 optical means
212 digital-to-analog-converting means
213 voltage control signal
214 voltage generating means

What is claimed is:

1. A device for detecting deposits in a reflection area inside a liquid-bearing system comprising an ultrasonic transducer for emitting an ultrasonic emission signal towards the reflection area and a first detection means for detecting an ultrasonic reflection signal obtained by reflection of the ultrasonic emission signal in the reflection area, wherein a second detection means is disposed in the reflection area, the second detection means being configured to detect a specific kind of deposit, wherein the second detection means is selected from the group consisting of an electrochemical biosensor, optical biosensor, electronic biosensor, piezoelectric biosensor or gravimetric biosensor, and light-addressable potentiometric sensor (LAPS), and wherein the second detection means is configured to generate a liveness detection signal comprising liveness-information about the deposits, extracellular acidification information of the deposits, information on a position dependent distribution of the deposits along a plane of main extension of a sensing surface of the second detection means, or a combination of information thereof.

2. The device according to claim 1, wherein the device comprises an analyzing unit configured to determine, a covering level of the deposits in the reflection area, whether the deposits contain living organisms in the reflection area, or both, wherein the covering level is a position dependent distribution of the deposits on the sensing surface of the second detection means.

3. The device according to claim 2, wherein the analyzing unit is configured to analyze the reflection signal in order to determine whether deposits are located in the reflection area, to determine the type of the deposit, the thickness of a layer of deposits in the reflection area or any combination thereof.

4. The device according to claim 1, wherein the second detection means is an electrochemical biosensor configured to generate the liveness detection signal depending on a measured electrochemical activity of the deposits.

5. The device according to claim 1, wherein the device has a first measuring unit comprising the ultrasonic transducer and the first detection means, wherein the device has a second measuring unit comprising the reflection area and the second detection means, wherein the first measuring unit and the second measuring unit are detachably connected to the liquid-bearing system wherein the first measuring unit and the second measuring units are located on opposite sides of the liquid-bearing system.

6. The device according to claim 1, wherein the device has a first reference measuring unit comprising a second ultrasonic transducer for emitting an ultrasonic emission signal towards a reflection area and a second, first detection means for detecting an ultrasonic reflection signal obtained by reflection of the ultrasonic emission signal in the reflection area, wherein the device has a second reference measuring unit comprising a second reflection area and a second, second detection means disposed in the second reflection area, the second detection means being configured to detect a specific kind of deposit, wherein the analyzing unit is configured to determine properties of the deposits in the reflection area depending on reference information provided by the first or second reference measurement unit or a combination thereof.

7. The device according to claim 1, wherein the second detection means is a light-addressable potentiometric sensor (LAPS) integrated into a chip card.

8. The device according to claim 7, wherein the analyzing unit is disposed on the chip card comprising the LAPS.

9. A method for detecting fouling and scaling deposits in a reflection area inside a liquid-bearing system, comprising a first step of emitting an ultrasonic emission signal towards the reflection area by an ultrasonic transducer, a second step of detecting an ultrasonic reflection signal obtained by reflection of the ultra-sonic emission signal in the reflection area by first detection means and a third step of detecting a specific kind of deposit by a second detection means disposed in the reflection area, wherein the second detection means is configured to generate a liveness detection signal and comprises a biosensor selected from the group consisting of an electrochemical biosensor, optical biosensor, electronic biosensor, piezoelectric biosensor, and gravimetric biosensor, and wherein the second detection means is configured to generate a liveness detection signal comprising liveness-information about the deposits, extracellular acidification information of the deposits, information on a position dependent distribution of the deposits along a plane of main extension of a sensing surface of the second detection means, or a combination of information thereof.

10. The method according to claim 9, wherein the liveliness detection signal in the third step comprises a first detection step, wherein the deposits in the reflection area are determined by a biological transducer of the biosensor, a second detection step, wherein a liveness detection signal is generated on an interaction between the deposits and a receptor of the biological transducer, a third detection step, wherein the liveness detection signal is received by an analyzing unit for determining a covering level of the deposits I the reflection area, whether the deposits contain living organisms in the reflection area, or both.

11. The method according to claim 10, wherein in the second step, the reflection signal is analyzed by the analyzing unit in order to determine whether deposits are located in the reflection area; determine the type of deposits in the reflection area; the thickness of a layer of deposits in the reflection area; or a combination thereof.

12. The method according to claim 9, wherein the second detection means is an electrochemical biosensor, wherein in the third step an electrochemical activity of the deposits is measured by the electrochemical biosensor and the liveness detection signal is generated depending on the measured electrochemical activity of the deposits.

13. The method according to claim 9, wherein in a fourth step, the liquid of the liquid-bearing system is treated depending on whether the deposits contain living organisms in the reflection area, the kind of deposits in the reflection area, the thickness of a layer of deposits in the reflection area, whether the deposits are located in the reflection area, or a combination thereof.

14. A device for detecting deposits in a reflection area inside a liquid-bearing system comprising an ultrasonic transducer for emitting an ultrasonic emission signal towards the reflection area and a first detection means for detecting an ultrasonic reflection signal obtained by reflection of the ultrasonic emission signal in the reflection area, wherein a second detection means is disposed in the reflection area, the second detection means being configured to detect a specific kind of deposit, and wherein the second detection means is a light-addressable potentiometric sensor (LAPS) integrated into a chip card.

* * * * *